United States Patent
Hessling-Von Heimendahl et al.

(10) Patent No.: US 10,151,708 B2
(45) Date of Patent: Dec. 11, 2018

(54) EROSION DETECTOR FOR AN EXTERIOR AIRCRAFT LIGHTING DEVICE AND EXTERIOR AIRCRAFT LIGHTING DEVICE COMPRISING THE SAME

(71) Applicant: Goodrich Lighting Systems GmbH, Lippstadt (DE)

(72) Inventors: Andre Hessling-Von Heimendahl, Koblenz (DE); Anil Kumar Jha, Lippstadt (DE)

(73) Assignee: GOODRICH LIGHTING SYSTEMS GMBH, Lippstadt (DE)

(*) Notice: Subject to any disclaimer, the term of this patent is extended or adjusted under 35 U.S.C. 154(b) by 0 days.

(21) Appl. No.: 15/080,653

(22) Filed: Mar. 25, 2016

(65) Prior Publication Data

US 2016/0282283 A1  Sep. 29, 2016

(30) Foreign Application Priority Data

Mar. 26, 2015 (EP) ..................... 15161066

(51) Int. Cl.
*G01N 21/00* (2006.01)
*G01N 21/958* (2006.01)
*B64D 47/06* (2006.01)
*G01N 21/47* (2006.01)
*B64D 45/00* (2006.01)

(52) U.S. Cl.
CPC ........... *G01N 21/958* (2013.01); *B64D 45/00* (2013.01); *B64D 47/06* (2013.01); *G01N 21/47* (2013.01); *B64D 2203/00* (2013.01); *G01N 2201/062* (2013.01); *G01N 2201/13* (2013.01)

(58) Field of Classification Search
None
See application file for complete search history.

(56) References Cited

U.S. PATENT DOCUMENTS

| | | | | |
|---|---|---|---|---|
| 3,652,863 A | * | 3/1972 | Gaskell | G01N 21/896 250/224 |
| 3,922,999 A | * | 12/1975 | Meginnis | G01N 3/567 116/208 |
| 3,947,131 A | * | 3/1976 | Karl | B60J 1/20 250/341.8 |
| 4,012,730 A | * | 3/1977 | Nicholls | G08B 13/1627 340/529 |

(Continued)

OTHER PUBLICATIONS

Extended European Search Report; Application No. 15161066.4-1504; dated Sep. 21, 2015; 6 pages.

*Primary Examiner* — Shawn Decenzo
*Assistant Examiner* — Jarreas C Underwood
(74) *Attorney, Agent, or Firm* — Cantor Colburn LLP

(57) ABSTRACT

An erosion detector for an exterior aircraft lighting device is configured for detecting the state of erosion of an at least partially transparent cover of an exterior aircraft lighting device and includes: at least one light source, which is configured for radiating light onto the at least partially transparent cover; at least one light detection element, which is configured for detecting light reflected by the at least partially transparent cover and for providing a corresponding detection signal; and an evaluation unit, which is configured for evaluating the detection signal for determining the state of erosion of the at least partially transparent cover.

18 Claims, 4 Drawing Sheets

(56) References Cited

U.S. PATENT DOCUMENTS

| | | | | |
|---|---|---|---|---|
| 4,323,785 A * | 4/1982 | McComb | G01N 21/896 | 250/302 |
| 4,652,745 A * | 3/1987 | Zanardelli | B60S 1/0822 | 250/227.25 |
| 4,782,331 A * | 11/1988 | Martens | B64D 15/20 | 340/580 |
| 4,797,660 A * | 1/1989 | Rein, Jr. | G08B 19/02 | 244/134 F |
| 4,808,813 A * | 2/1989 | Champetier | G01N 21/94 | 250/223 B |
| 5,117,120 A * | 5/1992 | Margaliot | G01T 5/02 | 250/472.1 |
| 5,497,100 A * | 3/1996 | Reiser | G01N 22/04 | 324/642 |
| 5,926,266 A * | 7/1999 | Dorundo | G01B 11/0608 | 356/237.2 |
| 6,010,095 A * | 1/2000 | Hackmeister | B64D 15/20 | 244/134 F |
| 6,031,456 A * | 2/2000 | Hanyuda | G08B 29/046 | 250/221 |
| 6,057,549 A * | 5/2000 | Castleman | G08B 17/12 | 250/339.14 |
| 7,091,855 B2 * | 8/2006 | Barrieau | G08B 17/00 | 340/540 |
| 7,288,750 B2 * | 10/2007 | Ewig | B60Q 1/00 | 250/205 |
| 7,312,713 B2 * | 12/2007 | Alfano | B64D 15/20 | 250/339.07 |
| 7,969,566 B2 * | 6/2011 | Smith | G01N 21/15 | 340/583 |
| 8,695,527 B2 * | 4/2014 | Edmond | B64D 45/00 | 116/208 |
| 9,488,598 B2 * | 11/2016 | Kim | G01N 21/958 | |
| 2006/0249663 A1 | 11/2006 | Ewig et al. | | |

* cited by examiner

EROSION DETECTOR FOR AN EXTERIOR AIRCRAFT LIGHTING DEVICE AND EXTERIOR AIRCRAFT LIGHTING DEVICE COMPRISING THE SAME

FOREIGN PRIORITY

This application claims priority to European Patent Application No. EP 15 161 066.4 filed Mar. 26, 2015, the entire contents of which is incorporated herein by reference.

TECHNICAL FIELD

The present invention relates to an erosion detector for an exterior aircraft lighting device and an exterior aircraft lighting device comprising such a detector.

BACKGROUND OF THE INVENTION

Almost all aircraft have exterior lights. In particular, large passenger air planes have a wide variety of exterior lights. Examples are navigation lights or position lights, beacon lights, anti-collision lights or strobe lights, wing lights, taxi lights, landing lights, runway turnoff lights, etc. Many of these lights are arranged on the exterior of the aircraft's wings fuselage, where they are exposed to the airstream flowing along the aircraft's exterior. Said airstream includes solid particles, as e.g. dust, causing wear of the lights' exterior, in particular of the lights exposed to a head-on airstream. In consequence, the lights' covers exposed to the airstream need to be regularly replaced in order to maintain the necessary illumination quality provided by the lights. If the cover is changed too late, the deteriorated illumination quality reduces flight safety; an early replacement of the cover, however, generates unnecessary costs.

It therefore would be beneficial to provide a detection device which reliably determines when it is necessary to change the light's cover due to wear.

SUMMARY

Exemplary embodiments of the invention include an exterior aircraft lighting device erosion detector which is configured for detecting the state of erosion of an at least partially transparent cover of an exterior aircraft lighting device. The exterior aircraft lighting device erosion detector comprises at least one light source configured for radiating light onto the at least partially transparent cover; at least one light detection element configured for detecting light reflected by the at least partially transparent cover and providing a corresponding detection signal; and an evaluation unit configured for evaluating the detection signal for determining the state of erosion of the at least partially transparent cover.

Exemplary embodiments of the invention also include an exterior aircraft lighting device comprising an at least partially transparent cover and an erosion detector according any of the exemplary embodiments of the invention, as described herein, wherein the erosion detector is attached to the at least partially transparent cover, in particular to the inside of the at least partially transparent cover.

Exemplary embodiments of the invention further include a method of evaluating the state of erosion of an at least partially transparent cover of an exterior aircraft lighting device, wherein the method comprises the steps of: radiating light onto the at least partially transparent cover; detecting light reflected by the at least partially transparent cover and providing a corresponding detection signal; and evaluating the detection signal for determining the state of erosion of the at least partially transparent cover. All features, advantages and modifications, described herein with respect to the exterior aircraft lighting device erosion detector, apply to the exterior aircraft device and to the method of evaluating the state of erosion of the at least partially transparent cover in an analogous manner. Analogous features and modifications are herewith disclosed by reference.

Evaluating the change of reflected light provides an easy, but reliable way of automatically determining the state of erosion of an at least partially transparent cover of an exterior aircraft lighting device, which in turn allows to change the cover when necessary and further avoids an unnecessary exchange of the cover when the quality of the cover is still good enough. This reduces the maintenance costs and grounding times of the aircraft. Uncertainties caused by human factors are avoided, and flight safety is enhanced.

In a further embodiment, the erosion detector further comprises a memory unit which is configured for storing at least one reference value. According to a further embodiment, the evaluation unit is configured for comparing an actual value of the detection signal with said reference value, which in particular may be a previously stored detection signal value. The evaluation unit may further be configured to issue an alarm signal, when the difference between the reference value and the actual value of the detection signal exceeds a predetermined threshold. In a particular embodiment, an alarm signal is triggered, if the actual value of the detection signal is less than 70% of the reference value.

The term actual value of the detection signal refers to a momentary value of the detection signal. The momentary values of the detection signal may be measured in set time intervals, e.g. via a sampling of the detection signal, or as a consequence of certain events, such as a powering up of the exterior aircraft lighting device. In general, a plurality of actual values are taken from the detection signal over time.

By comparing the actual value of the detection signal with a previously stored detection signal value, a deterioration of the cover's light transmitting quality due to wear can be reliably detected. A previously stored detection signal value, which has been generated in combination with a new cover, provides a well suited reference value allowing a reliable detection of the cover's wear.

The at least one light source of the erosion detector may be at least one LED.

In an embodiment, the erosion detector further comprises an alarm counter, which is configured for counting the alarm signals, and an indicator element which is configured to indicate erosion of the at least partially transparent cover when the number of alarms signals, in particular consecutive alarm signals, which have been counted by the alarm counter, exceeds a predetermined value. By indicating an erosion of the at least partially transparent cover only when the number of alarm signals, in particular the number of consecutive alarm signals, counted by the alarm counter exceeds a predetermined value, the risk of false alarms caused by a temporary soiling of the cover or a temporary dirt build-up on the cover, deteriorating the cover's transmission properties, is minimized.

According to a further embodiment, the erosion detector comprises at least one indicator element which is configured to indicate erosion of the at least partially transparent cover on the basis of the evaluation unit's evaluating of the detection signal. It is pointed out that other forms of determining erosion besides the alarm counter can be implemented, with the result of such determination being communicated by the at least one indicator element.

According to a further embodiment, the at least one indicator element may comprise or may consist of an optical indicator element. Optical signals are a very convenient form of communicating the state of erosion to the aircrew and/or to the ground personnel during aircraft inspection.

In an embodiment, the erosion detector further comprises a reset unit, which is configured for resetting the alarm counter when the difference between the actual value of the detection signal and the reference value, in particular the previously stored detection signal value, does not exceed a predetermined reset threshold for a predetermined number of tests, in particular for a predetermined number of consecutive tests. By resetting the alarm counter when the difference between the actual value of the detection signal and the previously stored detection signal value does not exceed a predetermined threshold for a predetermined number of tests, the risk of a false alarm causing an unnecessary early replacement of the light's cover is reduced even further. The predetermined reset threshold may be the same value as the predetermined threshold for issuing the alarm signal. However, it is also possible that the predetermined reset threshold is lower than the predetermined threshold for issuing the alarm signal, resulting in a kind of hysteresis between alarm and reset.

In an embodiment, the erosion detector further comprises a calibration unit which is configured for calibrating the evaluation unit, in particular by storing at least one reference value in the memory unit. The reference value in particular can be a detection signal value which has been detected at the beginning of using a new cover, in particular at the first activation operation(s) or during the first hour(s) of operation. In this way, this detection signal value, detected prior to or at the beginning of regular use of the exterior aircraft lighting device in the course of calibration, can be above-mentioned previously stored detection signal value.

Providing a calibration unit allows an automatic calibration of the detector avoiding the need of a manual re-calibration after the cover has been replaced, which reduces the cost and time for maintenance even further.

In an embodiment, the calibration unit is configured for storing an average of a plurality of detection signal values in the memory unit. Using an average of a plurality of detection signal values as a reference value, which is stored in the memory unit, enhances the quality of the detection even further and avoids false alarms caused by a single erroneous signal detected in the calibration phase.

In an embodiment, the erosion detector is configured to determine the state of erosion of the at least partially transparent cover every time the exterior aircraft lighting device is switched on. This allows a fast and reliable detection of a state in which the cover needs to be replaced.

In an embodiment, the erosion detector further comprises at least one indicator element, in particular an optical indicator element, which is configured for indicating a malfunction of a light unit of the exterior aircraft lighting device. This allows for a compact design of the detector providing information with respect to wear of the at least transparent cover as well as information related to a malfunction of the light unit, which is convenient for the user, such as aircrew or ground personnel, and reduces the costs for providing the respective detection and indication units.

In an embodiment, the at least one indicator element is visible from outside the aircraft when the exterior aircraft lighting device is installed at an aircraft, allowing the pilot as well as service and maintenance personnel to determine the state of the cover easily in the course of outside inspection of the aircraft. Alternatively or additionally, indicator elements may be provided within the aircraft's cockpit for allowing a visual inspection by the cockpit crew.

In an embodiment, the at least partially transparent cover has an arcuate shape, which in particular matches an aircraft's outer contour for optimizing the aerodynamic properties of the lighting device and the aircraft.

In an embodiment, the exterior aircraft lighting device is configured as a navigation or position light, a beacon light, an anti-collision or strobe light, a wing light, a taxi light, a landing light, or a runway turnoff light allowing an easy and fast maintenance of the respective light.

BRIEF DESCRIPTION OF DRAWINGS

Exemplary embodiments of the invention are described in greater detail below with reference to the enclosed figures.

DETAILED DESCRIPTION OF THE INVENTION

Figure 1:
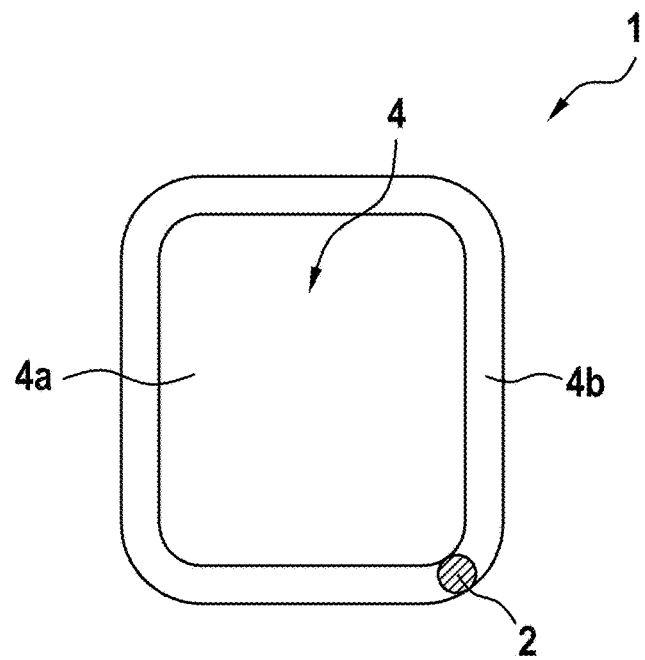
FIG. 1 shows a schematic plan view of an exterior aircraft lighting device comprising an erosion detector according to an exemplary embodiment of the invention.

FIG. 1 shows a schematic plan view of an exterior aircraft lighting device 1 comprising an erosion detector 2 according to an exemplary embodiment of the invention.

The lighting device 1, shown in FIG. 1, has a basically rectangular shape with rounded corners. The skilled person, however, will easily understand that embodiments of the invention may be employed in combination with other geometrical shapes, in particular including circular, elliptical, triangular and quadratic shapes, as well.

The side of the lighting device 1 facing the aircraft's exterior is covered by an at least partially transparent cover 4 comprising a transparent central area 4a allowing light, which is generated by at least one light source (not shown), to exit the lighting device 1, and an at least partially transparent circumferential external area 4b provided at the outer periphery of the cover 4.

An exemplary embodiment of an exterior aircraft lighting device erosion detector 2 is provided in a corner of said outer area 4b. The erosion detector 2 in particular may be fixed to the inside of the cover 4 by appropriate fixing means, in particular by an adhesive and/or a double sided adhesive strip. Of course, the erosion detector 2 may be located in other areas of the outer area 4b, as well.

Figure 2:
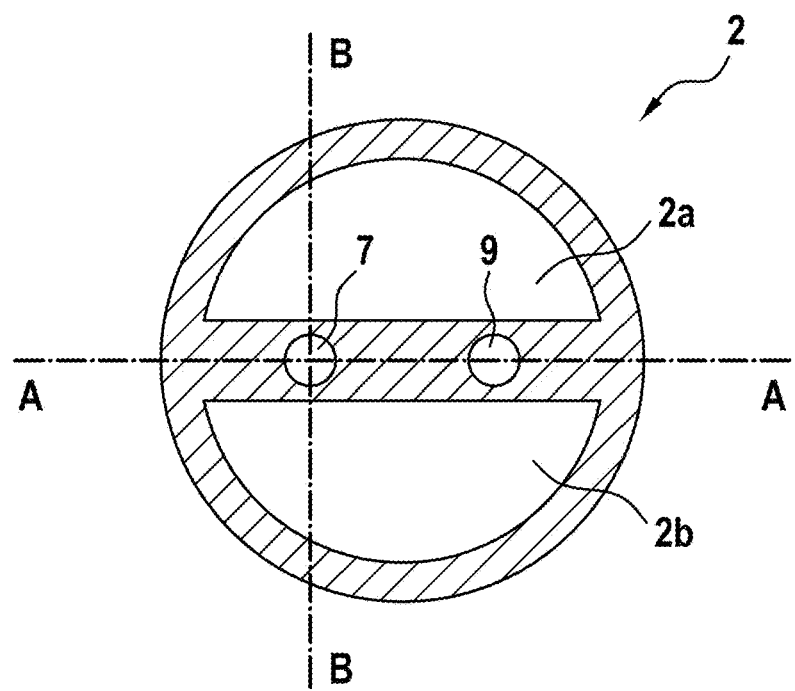
FIG. 2 shows a schematic plan view of the erosion detector as it is visible from the outside.

FIG. 2 shows a schematic plan view of the erosion detector 2, as it is visible from the outside. The erosion detector 2 shown in FIG. 2 has a circular shape, which, however, is only exemplary and the skilled person will easily understand that alternatively different shapes including rectangular and quadratic shapes may be employed, as well.

The detection device 2 comprises a first indication area 2a, which is shown in the upper portion of FIG. 2 and a second indication area 2b which is shown in the lower portion of FIG. 2, Said first indication area 2a is configured to light up in case erosion of the at least partially transparent cover 4 has been detected, as will be described in the following. The second indication area 2b, which is provided in the lower portion, is configured to light up in case a malfunction of the light unit, in particular a malfunction of at least one of the light unit's light sources, has been detected. The first and second indication areas 2a, 2b may be configured to light-up in different colors in order to allow an easy distinction between the events indicated by the respective indication areas 2a, 2b.

Two transparent circular windows 7, 9, which will be used for erosion detection, as will be described below, are provided between the first indication area 2a and the second indication area 2b. Again, it is noted that the shapes and the arrangement of the indication areas 2a, 2b and the windows 7, 9 shown in FIG. 2 are only exemplary and the skilled person will understand from the following description that they may be shaped and arranged differently without departing from the idea of the invention.

Figure 3:
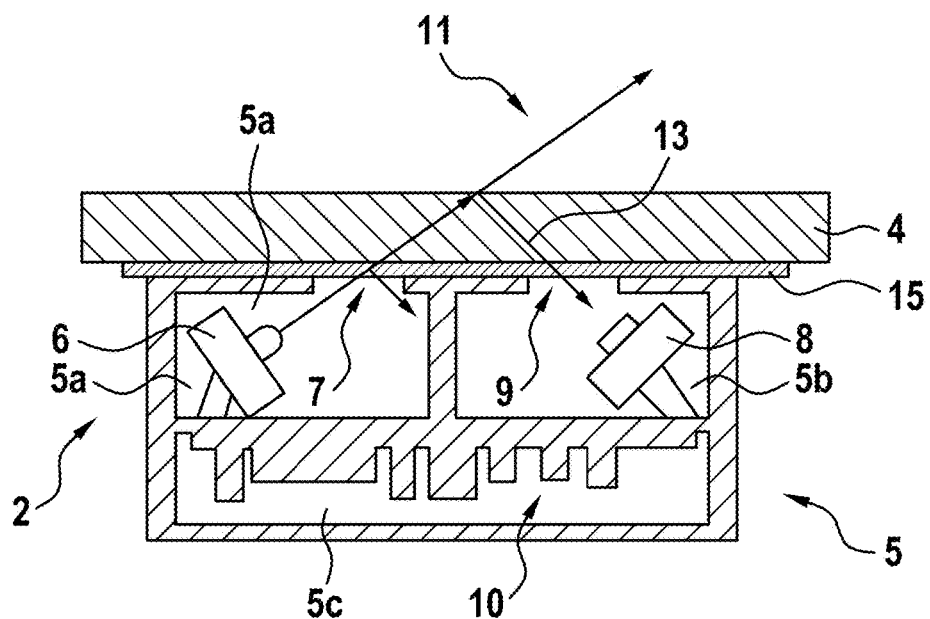
FIG. 3 shows a schematic cross-sectional view through the exemplary embodiment of the erosion detector.

FIG. 3 shows a schematic cross-sectional view through the exemplary embodiment of the erosion detector 2, which is taken along line A-A in FIG. 2.

The erosion detector 2 comprises a casing 5, which is arranged next to the at least partially transparent cover 4. The casing 5 in particular may be fixed to the cover 4 by appropriate fixing means including a transparent adhesive, in particular a transparent double sided adhesive strip 15 being arranged between the cover 4 and the casing 5.

In the cross-sectional view shown in FIG. 3, the interior of the casing 5 is divided into three chambers 5a, 5b, and 5c, the first two chambers 5a, 5b being arranged next to each other and sandwiched between the third chamber 5c and the adhesive strip 15 fixing the casing 4 to the cover 4.

At least one light source 6, in particular an LED, is provided within the first chamber 5a of the casing 5 and configured for radiating at least one light beam 11 through the first window 7, provided in the side of the first chamber 5a facing the cover 4, onto the cover 4.

Said light beam 11 is at least partially reflected by said cover 4, and a reflected beam 13 is radiated through the second window 9, provided in the side of the second chamber 5b facing the cover 4, onto at least one light detection element 8, provided in said second chamber 5b. Said light detection element 8 is configured for detecting the light reflected by the at least partially transparent cover 4 and for generating a corresponding electrical detection signal which is delivered to an evaluation unit 10, provided in the third chamber 5c of the casing 5, located below the first and second chambers 5a, 5b.

The functionality of the evaluation unit 10 will be described in detail further below with reference to FIGS. 6 and 7.

Figure 4:
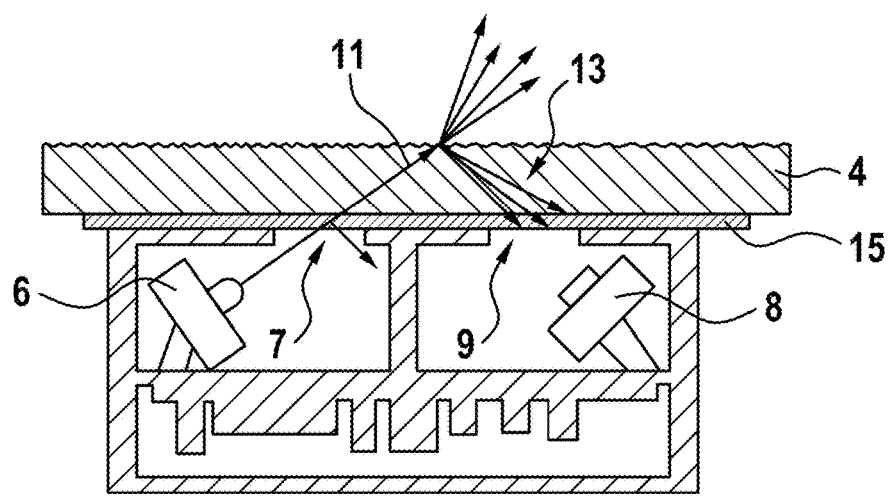
FIG. 4 shows a schematic cross-sectional view through the exemplary embodiment of the erosion detector.

FIG. 4 shows the same cross-sectional view as FIG. 3, including the at least partially transparent cover 4 and the erosion detector 2, in a situation in which the reflection properties of the at least partially transparent cover 4 are different, e.g. due to wear of the outer surface of the cover 4.

In this situation, the portion of light 13, which is reflected by the cover 4 towards the light detection element 8, is changed. Usually less light will be reflected onto the detection element 8 and in consequence a different (lower) detection signal level will be delivered from the detection element 8 to the evaluation unit 10. Said change of the detection signal allows the evaluation unit 10 to detect an erosion of the at least partially transparent cover 4.

Figure 5:
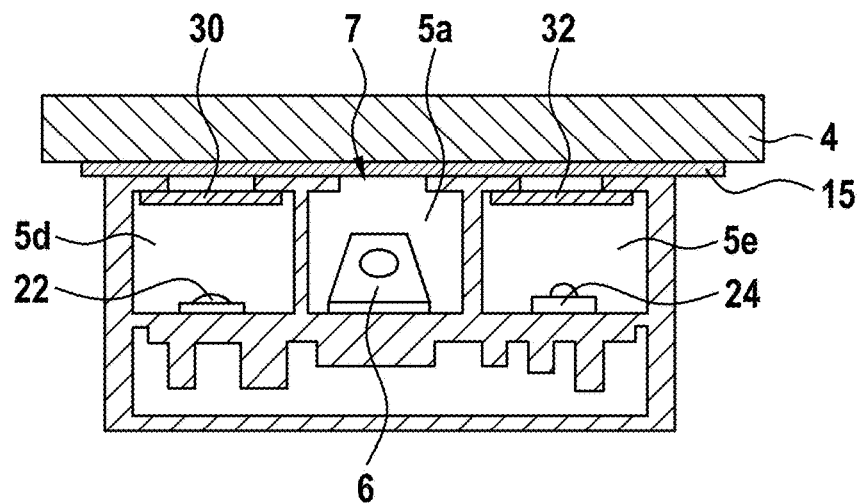
FIG. 5 shows a cross-sectional view through the exemplary embodiment of the erosion detector in a plane, which is arranged perpendicularly to the cross-sectional plane of FIGS. 3 and 4.

FIG. 5 shows a cross-sectional view through the exemplary embodiment of the erosion detector 2, taken along line B-B of FIG. 2, which is arranged orthogonally to line A-A.

In said view, the upper portion of the casing 5 of the erosion detector 2, which is next to the cover 4, is divided into three chambers, a central first chamber 5a housing the at least one light source 6, as already shown in FIGS. 3 and 4 (with the second chamber 5b of FIGS. 3 and 4 not being visible in said view), a fourth chamber 5d housing at least one first indicator element 22, which is triggered by the elevation unit 10 in case erosion of the at least partially transparent cover 4 has been detected, and a fifth chamber 5e housing at least one second indicator element 24, which is configured to be triggered in case a failure of the lighting device 1, in particular of at least one of its light sources, has been detected.

For providing colored indication signals, colored transparent elements 30, 32 may be arranged at the windows of the chambers 5d, 5e housing the indicator elements 22, 24. Additionally or alternatively, the indicator elements 22, 24 themselves may be configured to emit light of different colors, e.g. they may be embodied as LEDs emitting light of different colors.

Figure 6:
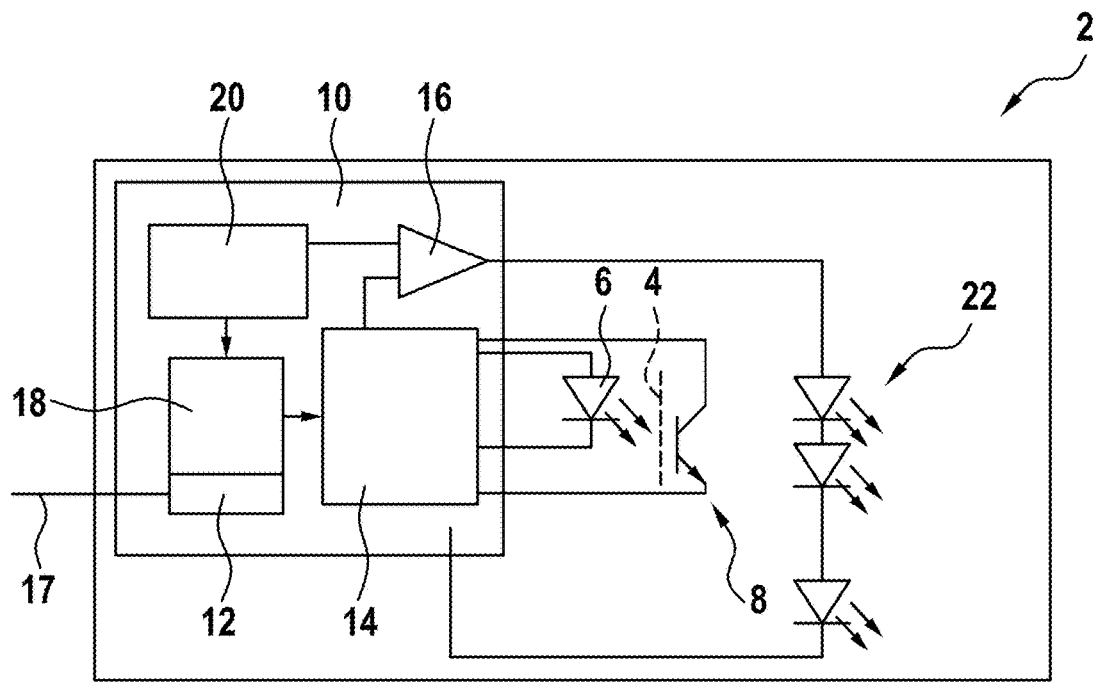
FIG. 6 shows a circuit diagram of an erosion detector according to an exemplary embodiment of the invention.

FIG. 6 is a circuit diagram of the electronic circuit of an erosion detector 2 according to an exemplary embodiment of the invention.

Electric power is supplied to the electronic circuit via a power line 17.

The at least one light source 6, the at least partially transparent cover 4 and the at least one light detection element 8 are schematically shown in the center of FIG. 6.

The at least one light source 6 is electrically connected to and driven by a driving and detection unit 14 which is also electrically connected to the light detection element 8 for evaluating the detection signal delivered by said at least one light detection element 8.

The evaluation unit 10 further comprises a memory unit 12 which is configured for storing at least one predetermined reference value to be compared with the actual values of the detection signal delivered by the at least one light detection element 8, in order to detect an erosion of the at least partially transparent cover 4. In particular, a considerable erosion is detected when the difference between the reference value and the actual value of the detection signal, delivered by the at least one light detection element 8, is above a predetermined threshold, which may also be stored within said memory unit 12.

The evaluation unit 10 further comprises a counter 20 and a calibration unit 18 which is configured for calibrating the erosion detector 2 by storing an appropriate reference value within the memory unit 12.

In an embodiment, the cycle counter 20 counts the activation operations of the exterior aircraft lighting device 1. A detection signal value provided by the at least one detection element 8 within a predetermined period of time and/or after a predetermined number of activation operations after a new cover 4 has been installed or an appropriate average of such detection signal values is stored within the memory unit 12 as the reference value. This is called the calibration phase of the erosion detector 2.

After the calibration phase has been finished, the detection signal values provided by the at least one detection element 8 are compared to said previously stored reference value, and an alarm is triggered in case the difference between the previously stored reference value and the actual value of the detection signal exceeds a predetermined threshold, i.e. a predefined maximum difference value. Said predetermined threshold may be an absolute threshold value or may be a threshold value that depends on the level of above-discussed reference value during calibration, e.g. a value corresponding to 30% of the reference value.

However, in order to avoid false alarms, which e.g. may be caused by moisture or dirt temporarily present on the at least partially transparent cover 4, an alarm is indicated, e.g. by lighting the first indication elements 22, only in case alarm signals are generated for a predetermined number of activation operations, in particular consecutive activation operations, which are also counted by the cycle counter 20.

In an optional embodiment, the indication of an alarm is switched-off again in case no alarm signals have been triggered for a predetermined number of consecutive activation operations, as this indicates that a false alarm has been triggered by a temporary degeneration of the quality of the cover 4, which is not present anymore.

Figure 7:
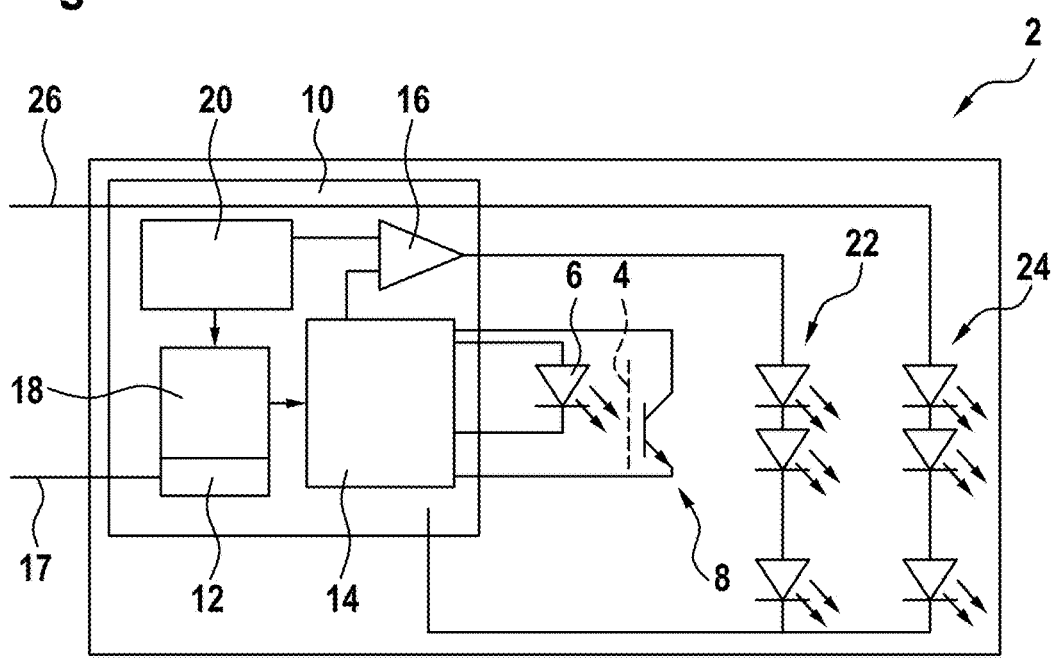
FIG. 7 shows a circuit diagram of an erosion detector according to an alternative embodiment of the invention.

FIG. 7 shows a circuit diagram of an alternative embodiment of the erosion detector 2 additionally comprising a string of second indicator elements 24, which are driven by an external alarm line 26 for indicating problems or malfunctions of the lighting device 1, in particular a malfunction of at least one of the lighting device's light sources, which are not shown in the figures.

Such a configuration, which combines the at least one first detection element 22 and the at least one second detection element 24 in a common detector 2, allows for a compact design providing information with respect to wear of the at least partially transparent cover as well as information related to a malfunction of the light unit, which is convenient for the user and reduces the costs for providing the respective detection and indication units.

By visually checking the indicator elements 22, 24 during outside inspection of the aircraft, a mechanic and/or pilot may easily determine whether it is necessary to change the at least partially transparent cover 4 due to wear or if a failure of the light unit has been detected. Alternatively or additionally, indicator elements 22, 24 may be located within the aircraft's cockpit for allowing a visual inspection by the cockpit crew.

While the invention has been described with reference to exemplary embodiments, it will be understood by those skilled in the art that various changes may be made and equivalents may be substituted for elements thereof without departing from the scope of the invention. In addition many modifications may be made to adopt a particular situation or material to the teachings of the invention without departing from the essential scope thereof. Therefore, it is intended that the invention not be limited to the particular embodiment disclosed, but that the invention include all embodiments falling within the scope of the following claims.

The invention claimed is:

1. An exterior aircraft lighting device erosion detector which is configured for detecting the state of erosion of an at least partially transparent cover of an exterior aircraft lighting device, the erosion detector comprising:
at least one light source configured for radiating light onto the at least partially transparent cover;
at least one light detection element configured for detecting light reflected by the at least partially transparent cover and providing a corresponding detection signal; and
an evaluator configured for evaluating the detection signal for determining the state of erosion of the at least partially transparent cover by comparing an actual value of the detection signal with a reference value;
wherein the evaluator is configured to issue an alarm signal, when the difference between the reference value and the actual value of the detection signal exceeds a predetermined threshold;
wherein the erosion detector further comprises a counter which is configured for counting the alarm signals, which relate to a plurality of actual values taken from the detection signal over time with the at least one light source and the at least one light detection element having a set position with respect to the at least partially transparent cover; and
wherein the erosion detector further comprises at least one indicator element which is configured to indicate erosion of the at least partially transparent cover when the number of alarms counted by the counter exceeds a predetermined value.

2. The exterior aircraft lighting device erosion detector of claim 1, wherein the erosion detector further comprises a memory configured for storing the reference value.

3. The exterior aircraft lighting device erosion detector of claim 1, wherein the reference value is a previously stored detection signal value.

4. The exterior aircraft lighting device erosion detector of claim 1, wherein the at least one indicator element is an optical indicator element.

5. The exterior aircraft lighting device erosion detector of claim 3, further comprising a reseter, which is configured for resetting the counter when the difference between the actual value of the detection signal and the previously stored detection signal value does not exceed a predetermined reset threshold for a predetermined number of tests.

6. The exterior aircraft lighting device erosion detector of claim 2, further comprising a calibrator which is configured for calibrating the evaluator.

7. The exterior aircraft lighting device erosion detector of claim 6, wherein the calibrator is configured for storing an average of a plurality of detection signal values in the memory.

8. The exterior aircraft lighting device erosion detector of claim 1, wherein the erosion detector is configured to determine the state of erosion of the at least partially transparent cover every time the exterior aircraft lighting device is switched on.

9. The exterior aircraft lighting device erosion detector of claim 1, wherein the erosion detector further comprises an optical indicator element for indicating a malfunction of a light emitter of the exterior aircraft lighting device.

10. An exterior aircraft lighting device comprising:
an at least partially transparent cover,
at least one light emitter, which is configured for emitting light through the at least partially transparent cover, and
an erosion detector according to claim 1,
wherein the erosion detector is attached to the at least partially transparent cover.

11. The exterior aircraft lighting device of claim 10, wherein, when the exterior aircraft lighting device is installed at an aircraft, at least one indicator element is visible from outside the aircraft.

12. The exterior aircraft lighting device of claim 10, wherein the at least partially transparent cover has an arcuate shape.

13. A method of evaluating the state of erosion of an at least partially transparent cover of an exterior aircraft lighting device, comprising the steps of:
- radiating light onto the at least partially transparent cover;
- detecting light reflected by the at least partially transparent cover and providing a corresponding detection signal; and
- evaluating the detection signal for determining the state of erosion of the at least partially transparent cover by comparing an actual value of the detection signal with a reference value;
- issuing an alarm signal, when the difference between the reference value and the actual value of the detection signal exceeds a predetermined threshold;
- counting the alarm signals, which relate to a plurality of actual values taken from the detection signal over time with the at least one light source and the at least one light detection element having a set position with respect to the at least partially transparent cover; and
- indicating erosion of the at least partially transparent cover when the number of counted alarms exceeds a predetermined value.

14. The exterior aircraft lighting device erosion detector of claim 3, further comprising a reseter, which is configured for resetting the counter when the difference between the actual value of the detection signal and the previously stored detection signal value does not exceed a predetermined reset threshold for a predetermined number of consecutive tests.

15. The exterior aircraft lighting device erosion detector of claim 6, wherein the calibrator is configured for calibrating the evaluator by storing a detection signal value as the reference value in the memory.

16. The exterior aircraft lighting device according to claim 10, wherein the erosion detector is attached to an inside of the at least partially transparent cover.

17. The exterior aircraft lighting device of claim 12, wherein the arcuate shape matches an aircraft's outer contour.

18. The exterior aircraft lighting device of claim 10, wherein the exterior aircraft lighting device is configured as a navigation or position light, a beacon light, an anti-collision or strobe light, a wing light, a taxi light, a landing light, or a runway turnoff light.

* * * * *